May 18, 1965 R. H. RASMUSSEN Plant Pat. 2,513

BLUEGRASS PLANT

Filed July 23, 1963 3 Sheets-Sheet 1

INVENTOR.

ROSS HANS RASMUSSEN

BY

Merriam, Smith & Marshall

ATTORNEYS

BLUEGRASS PLANT

Filed July 23, 1963 3 Sheets-Sheet 2

INVENTOR.
ROSS HANS RASMUSSEN
BY
Merriam, Smith & Marshall
ATTORNEYS

INVENTOR.
ROSS HANS RASMUSSEN
BY
Merriam, Smith & Marshall
ATTORNEYS

United States Patent Office

Plant Pat. 2,513
Patented May 18, 1965

2,513
BLUEGRASS PLANT

Ross Hans Rasmussen, Hooper, Nebr.

Filed July 23, 1963, Ser. No. 297,167
1 Claim. (Cl. Plt.—88)

The present invention relates to a new and distinct bluegrass plant which was discovered by myself in a pasture on a farm in Dodge County, Nebraska.

When I discovered this plant, it was mature and bore ripe seed heads. Because of the distinctive color and size of the seed heads, and shorter than expected plant height, I was immediately attracted to further examine this plant. Upon closer examination, it appeared that this plant possessed a combination of characteristics previously unobserved by me in other bluegrasses. Despite the numerous drouths and hot weather incident to this area, this plant had persisted where other, native bluegrasses had not.

I have asexually reproduced this new plant with row plantings of rhizomes, and the asexual reproductions have run true to the originally discovered plant in all respects. I have harvested and planted seed from the new variety and find that the plant demonstrates a high degree of apomixism.

Critical examination of the new grass under turf conditions reveals the following desirable qualities:

(1) Leaves of relatively fine texture, (2) Ability to withstand limited moisture conditions and high soil and air temperatures prevalent in this area of the country, (3) Highly competitive with respect to other grasses and herbs, and (4) Firm, hard soil surface which minimizes disease infestation and makes it suitable for hard use areas such as football fields, golf fairways and lawns.

In the accompanying drawings of my grass:

FIGURE 1 is a dorsal view of a typical spikelet, enlarged about 4.8 times normal size. Reference number 1 indicates the pedicel; numbers 2 and 3 indicate the glumes with 3 being the first glume reduced in size as compared to 2; number 4 indicates fertile florets; and number 5 indicates the terminal floret, usually reduced and sterile.

Figure 1:
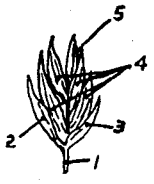
Figure 2:
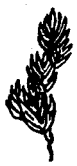
FIGURE 2 illustrates a cluster of spikelets, enlarged about 2.4 times normal size. Usually two such clusters make up the total spikelets per individual branch of the inflorescence.
Figure 3:
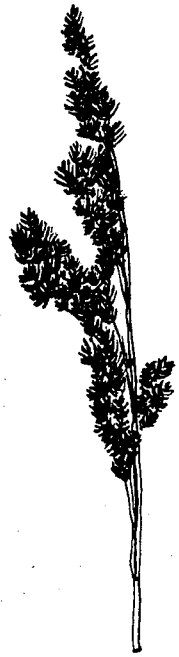
FIGURE 3 shows an inflorescence of approximately 1.2 times normal size. This illustrates the somewhat compact panicle characteristic of this new plant.
Figure 4:
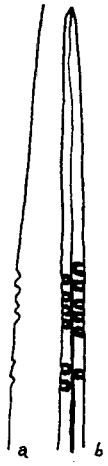
FIGURE 4 illustrates a culm leaf blade, about 1.2 times normal size, showing the deformation associated with these blades. View "*a*" depicts the line seen when viewing the edge of the blade from the side; view "*b*" the same leaf viewed from the front perpendicular to the central nerve of the blade.
Figure 5:
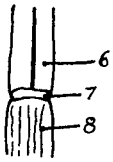

FIGURE 5 is a sketch of the ligule area of the leaf, about 2.4 times normal size. Number 6 designates that portion of the blade adjacent to the ligule; number 7 the ligule itself, scarious, uniform in height and nearly entire; and number 8 the sheath portion of the leaf adjacent to the ligule, here depicted unrolled.

Figure 6:
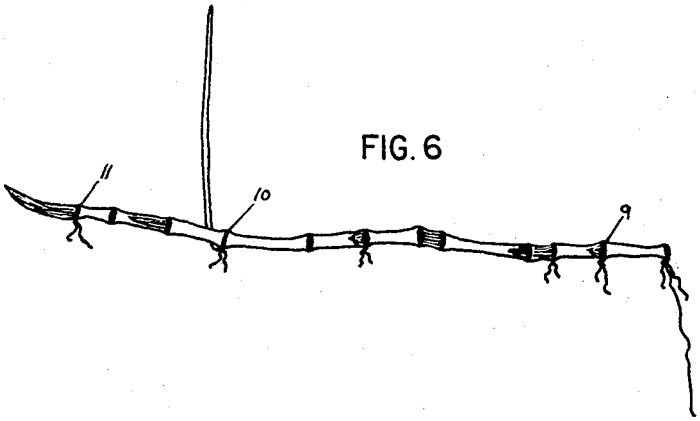

FIGURE 6 illustrates a typical rhizome, about 2.4 times normal size. Particularly noticeable is the nonuniformity of internode length and ability of nodes to produce roots and/or shoots. Number 9 indicates a node with root growth and fragments of scales remaining attached at the node; number 10 shows a node which has produced a new shoot; and number 11 is the terminal node and scale from which a new plant can develop or further growth of the rhizome occur.

Figure 7:
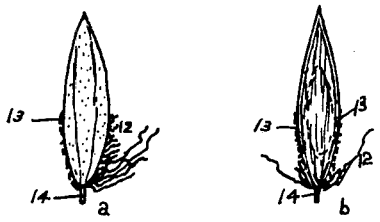

FIGURE 7 depicts a fertile floret about 12 times normal size. View "*a*" is of the dorsal side showing the punctate lemma and indistinct nerves. View "*b*" is of the ventral side of the floret showing the enclosed membranaceous palea. Numbers for both views designate the same structure. Number 14 indicates the rachilla; number 12 indicates the sericeous webbing originating about the juncture between rachilla and lemma and the prominent midnerve of the lemma; and number 13 indicates shorter webbing which is found on the outer edges of the lemma.

Figure 8:
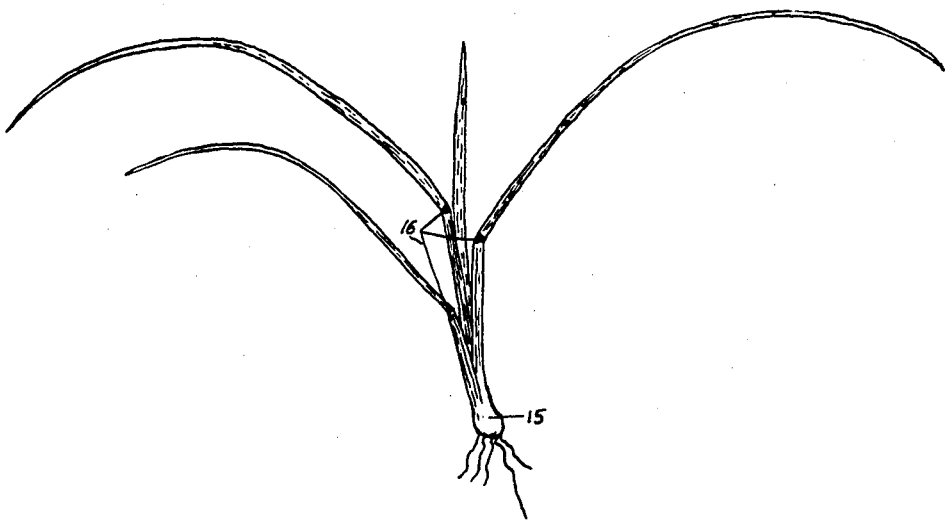

FIGURE 8 represents a vegetative plant about 0.6 times normal size. Number 15 indicates the crown area of the plant; and number 16 indicates the readily noticeable collar at the junction of sheath and blade.

The following is a detailed description of my new grass expressed in appropriate botanical terminology:

*Parentage.*—Unknown.

*Classification.*—Typical of the Poa family, probably most closely related to *Poa pratensis* (Kentucky bluegrass). It differs from this species, however, in being smaller throughout, having an erect, more compact panicle, and by having extremely deep, penetrating and more numerous rhizomes. The mature panicles have a distinct deeper tan color. The compactness of the seed head is characteristic of *Poa compressa* (Canada bluegrass). However, this new grass is not flattened in the culm, has a uniformly branched panicle and inhabits sites not characteristic of *Poa compressa*. The uniformity of plants within a planting of this new grass is something not readily expected from a species of Poa.

*Growth.*—Perennial; rapid seed germination and seedling growth; recovers readily from handling as sod; establishes from sod strips rapidly; responds readily to normal lawn care; withstands adverse moisture and temperature conditions. Produces a tough, resilient sod from numerous vigorous rhizomes.

*Leaves.*—Ascending tufts; 10 to 30 cm. in length; 3 to 5 mm. in width; folded to flat; somewhat geniculate culms arise from among tufts of leaves, extending 5 to 15 cm. above the tufted leaves; the ligule is of medium length (1.5 to 2.5 mm.) and obtuse; sheaths and blades are glabrous, the sheath about two-thirds the length of the internode; blades end in cucullate tip. Culm blades deformed. Appears to be an impression of seed head prior to emergence.

*Inflorescence.*—The simple culm produces a panicle inflorescence 2.5 to 5.5 cm. in length, mostly compressed, except at anthesis. During anthesis to maturity the inflorescence has a distinct purplish-green cast, and on maturity has a tan color deeper than is characteristic of the more common Poa species. Branching occurs at approximately 2 cm. intervals from the tip down, having usually 4 branchings. There are 2 to 4 spikelets per peduncle. Spikelets have 2 to 5 florets, the uppermost usually imperfect (reduced and sterile). Glumes are keeled, the first shorter than the second, awnless, usually 5-nerved, the intermediate nerves sometimes obscure. The paleas are membranaceous, tightly embracing the caryopsis.

Lemmas mostly 5-nerved, hairy, with tufts of long hairs at the rachilla also tightly embracing the caryopsis and palea where the two are in contact. Pedicels are 5 mm. in length.

I claim:

A new and distinct variety of bluegrass plant substantially as herein disclosed and described, characterized by its ability to produce a plant of dense, close foliage with unusual ability to withstand adverse weather conditions, having leaves of relatively fine texture, and a deep root system contributing to a firm, hard soil surface which minimizes disease infestation and makes the turf suitable for hard use areas such as football fields, golf fairways and lawns on which there is heavy traffic and which, because of the close and dense growth of the plant, is able to withstand close cutting without damage to normal growth.

No references cited.

ABRAHAM G. STONE, *Primary Examiner.*